United States Patent [19]

Inoue et al.

[11] Patent Number: 4,714,702
[45] Date of Patent: Dec. 22, 1987

[54] QUINAZOLINONE DERIVATIVE

[75] Inventors: Ichizo Inoue, Kawanishi; Toyonari Oine, Nara; Yoshihisa Yamada, Kyoto; Ryuichi Ishida, Suita; Takashi Ochiai, Kobe, all of Japan

[73] Assignee: Tanabe Seiyaku Co., Ltd., Osaka, Japan

[21] Appl. No.: 888,631

[22] Filed: Jul. 21, 1986

Related U.S. Application Data

[63] Continuation of Ser. No. 564,006, Dec. 21, 1983, abandoned.

[30] Foreign Application Priority Data

Jan. 13, 1983 [JP] Japan .................................. 58-4707

[51] Int. Cl.[4] .................... A61K 31/505; C07D 239/90
[52] U.S. Cl. .................................. 514/259; 544/290; 564/166
[58] Field of Search .................... 544/290; 514/259

[56] References Cited

FOREIGN PATENT DOCUMENTS 2247246 5/1975 France .

OTHER PUBLICATIONS

Inoue et al., "Chemical Abstracts", vol. 83, 1975, col. 58867t.
Inoue et al., "Chemical Abstracts", vol. 86, 1977, col. 86:89883m.
Inoue et al., "Chemical Abstracts", vol. 86, 1977, col. 86:121360b.
Tani et al., "Chemical Abstracts", vol. 90, 1979, col. 90:80710c.
Furuuchi et al., "Chemical Abstracts", vol. 99, 1983, col. 99:115495b.
Tani et al., "Jour. Med. Chem", vol. 22, No. 1, 1979, pp. 95-99.
Tani et al., "Chemical Abstracts", vol. 93, 1980, col. 93:26374v.
Otkusa et al., "Chemical Abstracts", vol. 100, 1984, col. 100:29262f.

Primary Examiner—Glennon H. Hollrah
Assistant Examiner—James H. Turnipseed
Attorney, Agent, or Firm—Jordan B. Bierman

[57] ABSTRACT

A quinazolinone derivative of the formula:

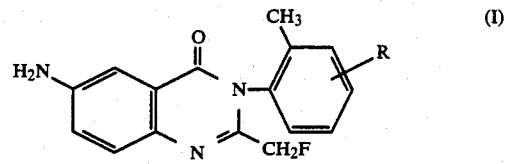

wherein R is lower alkyl, lower alkoxy or halogen. Said quinazolinone derivative (I) or a pharmaceutically acceptable acid addition salt thereof is useful as central muscle relaxants.

2 Claims, No Drawings

QUINAZOLINONE DERIVATIVE

This application is a continuation of application Ser. No. 564,006, filed 12/21/83, now abandoned.

This invention relates to a novel quinazolinone derivative and a process for preparing the same. More particularly, it relates to a compound of the formula:

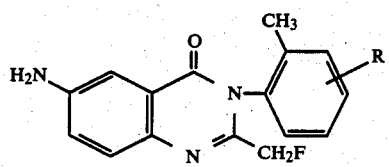

wherein R is lower alkyl, lower alkoxy or halogen, or a pharmaceutically acceptable acid addition salt thereof.

The new quinazolinone derivative (I) of the present invention and a pharmaceutically acceptable acid addition salt thereof are useful as central muscle relaxants. For example, the muscle relaxing activity of 2-fluoromethyl-3-(2-methyl-4-chlorophenyl)-6-amino-4(3H)-quinazolinone of the present invention when examined by the rotating rod method (mice) is about 36.6 times stronger than that of Mephenesin (chemical name: 3-(o-tolyloxy)-1,2-propanediol). Moreover, the compound (I) of the invention shows greater safety as compared with said known muscle relaxant. For example, the safety margin (i.e., the potency ratio of the acute toxicity to the muscle relaxing activity) of 2-fluoromethyl-3-(2-methyl-4-chlorophenyl)-6-amino-4(3H)-quinazolinone of the invention is about 12.7 times as high as that of Mephenesin.

Among the compounds of the present invention, a preferred subgenus includes those of the formula (I) in which R is lower alkyl such as methyl, ethyl, propyl or butyl; lower alkoxy such as methoxy, ethoxy, propoxy or butoxy; and halogen such as fluorine, chlorine or bromine. More preferred subgenus includes those of the formula (I) in which R is methyl, methoxy, fluorine, chlorine or bromine and is in the 3rd-, 4th- or 5th-position of phenyl group. Further preferred subgenus include those of the formula (I) in which R is methyl, fluorine or chlorine and is in the 3rd-, 4th- or 5th-position of phenyl group. Most preferred subgenus includes those of the formula (I) in which R is chlorine and is in the 4th-position of phenyl group.

According to the present invention, the compound (I) can be prepared according to the following reaction scheme.

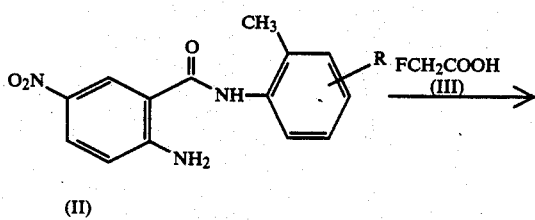

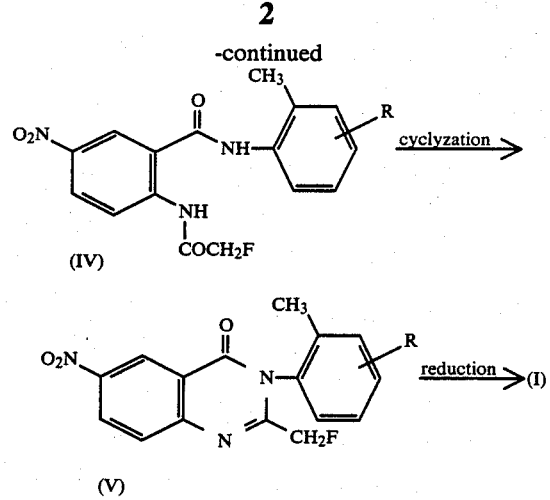

wherein R is the same as defined above.

Namely, the compound (I) of the invention can be prepared by condensing the compound (II) with fluoroacetic acid (III) or a reactive derivative thereof, subjecting the resultant compound (IV) to intramolecular cyclization, and then reducing the thus-obtained compound (V).

The condensation reaction of the compound (II) with the compound (III) or a reactive derivative thereof can be accomplished by conventional methods. For example, the condensation of compound (II) with compound (III) is conducted in the presence of a dehydrating agent in a solvent. N,N'-dicyclohexylcarbodiimide, N,N'-carbonyl-diimidazole and the like are preferably employed as the dehydrating agent. Dimethylformamide and dimethylacetamide are suitable as the reaction solvent. It is preferred to carry out the reaction at a temperature of 15° to 100° C. Alternatively, the condensation of compound (II) wit the reactive derivative of fluoroacetic acid (III) is conducted in the presence of an acid acceptor in a solvent. Organic bases such as pyridine and triethylamine, and inorganic bases such as alkali metal carbonate or bicarbonate (e.g., sodium carbonate, potassium carbonate, sodium bicarbonate or potassium bicarbonate) are employed as the acid acceptor. Tetrahydrofuran, dioxane, dimethylformamide and the like are suitable as the reaction solvent. Preferred examples of the reactive derivative of fluoroacetic acid (III) include the corresponding acid anhydride and acid halide (e.g., chloride, bromide). When fluoroacetic acid anhydride is employed, it is preferred to carry out the condensation at a temperature of 15° to 100° C. On the other hand, when fluoroacetyl halide is employed, it is preferred to carry out the condensation at a temperature of −20° to 50° C., especially 0° to 20° C.

The intra-molecular cyclyzation of the compound (IV) is conducted in the presence of boron trifluoride (etherate) or acetic anhydride in a solvent under heating. Acetic acid, toluene, dioxane and the like are suitable as the solvent. It is preferred to carry out the reaction at a temperature of 90° to 120° C.

The reduction of the compound (V) is accomplished by treating it with a reducing agent in a solvent. Suitable examples of the reducing agent include a mixture of multivalent metal or multivalent metal chloride and an acid. Examples of multivalent metal include, for example, tin, iron, zinc and the like. Preferred example of the corresponding metal chloride are stannous chloride. Suitable examples of the acid include mineral acids such as hydrobromic acid or hydrochloric acid, and organic acids such as acetic acid or propionic acid. Water, methanol, ethanol, acetic acid, ether, tetrahydrofuran or a mixture thereof are suitable as the solvent. It is preferred to carry out the reaction at a temperature of 0° to 80° C., especially 0° to 40° C. Alternatively, the reduction of the compound (V) may be conducted by catalytic hydrogenation thereof. This catalytic hydrogenation is carried out in the presence of a catalyst in a hydrogen gas atmosphere in a solvent. Examples of the catalyst include palladium-charcoal, palladium-barium sulfate, palladium black, Raney nickel, Raney cobalt, platinum dioxide and so forth. Acetic acid, ethanol, tetrahydrofuran and the like are suitable as the solvent. It is preferred to carry out the reaction at a temperature of 10° to 100° C., especially 30° to 60° C., under atmospheric pressure.

As mentioned hereinbefore, the compound (I) of the present invention shows potent muscle relaxing activity and is useful for the therapeutic treatment of abnormal elevation of muscle tonus resulting from cervicobranchial syndrome and lumbago, spastic paralysis, neurogenic bladder and so forth.

Compound (I) of the present invention can be used pharamaceutically either in the form of free base or a salt thereof. Pharmaceutically acceptable acid addition salt of the compound (I) includes, for example, hydrochloride, hydrobromide, perchlorate, nitrate, sulfate, phosphate, methanesulfonate, ethanesulfonate, benzenesulfonate, p-toluenesulfonate and sulfanilate. A daily dose of compound (I) of the present invention will vary depending on severity of disease, age, weight or conditions of patients and other factors. A suitable daily dose of compound (I) or a salt thereof may be about 0.05 to about 5.0 mg/kg, especially 0.1 to 2.0 mg/kg. Further, compound (I) or a salt thereof may be used in the form of a pharmaceutical preparation containing the same compound in conjunction or admixture with a pharmaceutical excipient suitable for oral or parenteral administration. Suitable excipients include, for example, starch, lactose, gelatin, glucose, sodium chloride, magnesium stearate, talcum, vegetable oil, benzylalcohol, gums and other known medicinal excipients. The pharmaceutical preparations may be in solid form such as tablets, pills, capsules or suppositories; or in liquid form such as solutions, suspensions or emulsions. They may be sterillized and/or may further contain auxiliaries such as stabilizing, wetting or emulsifying agent.

Concomitantly, the starting compound (II) of the invention may be prepared, for example, by reacting 5-nitroisatoic anhydride of the formula:

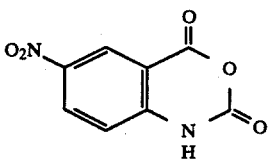

with an aniline derivative of the formula:

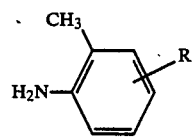

wherein R is the same as defined above.

Practical and presently-preferred embodiments of the present invention are illustratively shown in the following Examples. Throughout the specification and claims, the term "lower alkyl" and "lower alkoxy" should be interpreted as referring to alkyl and alkoxy having one to four carbon atoms.

EXPERIMENT (A) Muscle relaxing activity (the rotating rod method)

A test compound dissolved or suspended in an aqueous 0.5% carboxymethylcellulose sodium salt solution was administered orally to a group of three male mice (ddY-strain, body weight: 18–20 g). After administration of the test compound, the mice were placed on a rotating rod (3.5 cm in diameter, 7.5 r.p.m.) at intervals, and the number of mice which fell out of the rod at least twice within one minute was counted. The 50% effective dose ($ED_{50}$) of the test compound was calculated therefrom according to the probit method.

(B) Acute toxicity

A test compound dissolved or suspended in an aqueous 0.5% carboxymethylcellulose sodium salt solution was administered orally to a group of six male mice (ddY-strain, body weight: 18–20 g). The 50% lethal dose ($LD_{50}$) of the test compound was calculated according to the probit method from the number of mice which died within a period of 72 hours after administration.

The results are shown in the following Table.

TABLE

| Test compound | Muscle relaxing activity $ED_{50}$ (mg/kg) | Acute toxicity $LD_{50}$ (mg/kg) | Safety margin ($LD_{50}/ED_{50}$) |
|---|---|---|---|
| 1. | 13.6 | 701.9 | 51.6 |
| Mephenesin | 497.8 | 2020.0 | 4.06 |

| Test compound | Chemical name |
|---|---|
| 1. | 2-fluoromethyl-3-(2-methyl-4-chlorophenyl)-6-amino-4(3H)—quinazolinone |

EXAMPLE 1

(1) 4.0 g of N-(2-amino-5-nitrobenzoyl)-2,4-dimethylaniline and 2.36 g of pyridine are dissolved in 50 ml of tetrahydrofuran, and 2.18 g of fluoracetyl chloride are added dropwise thereto under ice-cooling. The mixture is then stirred at room temperature for 5 hours. The mixture is concentrated under reduced pressure to remove tetrahydrofuran, and 100 ml of water are added to the residue. Crystalline precipitates are collected by filtration and recrystallized from a mixture of dimethylformamide and ethanol (1:2). 4.3 g of N-(2-fluoroacetamido-5-nitrobenzoyl)-2,4-dimethylaniline are obtained as colorless needles.

M.p. 227°–229° C.

NMR (DMSO-$d_6$) δ: 2.24 (3H, s), 2.32 (3H, s), 5.09 (2H, d, J=46 Hz), 6.9–7.4 (3H, broad s), 8.48 (1H, d, d, J=9 Hz, J=3 Hz), 8.82 (1H, d, J=9 Hz) 8.95 (1H, d, J=3 Hz), 10.60 (1H, s) 12.18 (1H, broad s).

(2) 4.0 g of N-(2-fluoroacetamido-5-nitrobenzoyl)-2,4-dimethylaniline are added to a mixture of 30 ml of acetic acid and 3.5 g of boron trifluoride etherate, and the mixture is stirred under heating at 100° to 105° C. for 30 minutes. The mixture is cooled and concentrated under reduced pressure to remove acetic acid. 50 ml of water are added to the residue, and the mixture is neutralized with potassium carbonate. The mixture is extracted with chloroform, and the extract is washed with water and dried. The chloroform solution is concentrated under reduced pressure to remove solvent. Isopropanol is added to the residue, and crystalline precipitates are collected by filtration. The thus-obtained crystals (3.0 g, M.p. 198°–200° C.) are recrystallized from a mixture of dimethylformamide and ethanol (1:2). 2.6 g of 2-fluoromethyl-3-(2,4-dimethylphenyl)-6-nitro-4(3H)-quinazolinone are obtained as colorless prisms.

M.p. 200°–202° C.

NMR (CDCl$_3$) δ: 2.11 (3H, s), 2.44 (3H, s), 4.96 (2H, d, J=4.7 Hz), 6.9–7.4 (3H, m), 7.94 (1H, d, J=9 Hz), 8.58 (1H, d, d, J=9 Hz, J=3 Hz), 9.12 (1H, d, J=3 Hz).

(3) 2.0 g of 2-fluoromethyl-3-(2,4-dimethylphenyl)-6-nitro-4(3H)-quinazolinone are suspended in 35 ml of methanol, and a solution of 5.4 g of stannous chloride dihydrate in 5 ml of conc. hydrochloric acid is added dropwise thereto under ice-cooling and stirring. Then, the mixture is stirred at room temperature overnight. The mixture is concentrated under reduced pressure to remove methanol, and water is added to the residue. The aqueous mixture is neutralized with sodium bicarbonate, and chloroform is added thereto. After stirring the mixture, insoluble materials are filtered off. The chloroform solution is separated from the filtrate and concentrated under reduced pressure to give a crystalline residue. The thus-obtained crystals (1.4 g) are recrystallized from isopropanol. 1.2 g of 2-fluoromethyl-3-(2,4-dimethylphenyl)-6-amino-4(3H)-quinazolinone are obtained as pale yellow prisms.

M.p. 175°–177° C.

NMR (DMSO-d$_6$) δ: 2.10 (3H, s), 2.42 (3H, s), 3.85 (2H, broad s), 4.93 (2H, d, J=47 Hz), 6.9–7.3 (4H, m), 7.58 (1H, d, J=3 Hz), 7.63 (1H, d, J=8 Hz).

EXAMPLE 2

(1) 3.3 g of N-(2-amino-5-nitrobenzoyl)-2-methyl-4-chloroaniline and 1.6 g of pyridine are dissolved in 60 ml of tetrahydrofuran, and 1.93 g of fluoroacetyl chloride are added dropwise thereto under ice-cooling and stirring. The mixture is stirred for 30 minutes under ice-cooling and further stirred at room temperature for 2 hours. The mixture is concentrated under reduced pressure to remove tetrahydrofuran. Water is added to the residue and crystalline precipitates are collected therefrom. The crystals are recrystallized from a mixture of dimethylformamide and ethanol (1:3). 3.6 g of N-(2-fluoroacetamido-5-nitrobenzoyl)-2-methyl-4-chloroaniline are obtained as colorless needles.

M.p. 238°–239° C.

NMR (DMSO-d$_6$) δ: 2.28 (3H, s), 5.07 (2H, d, J=45 Hz), 7.23–7.59 (3H, m), 8.42 (1H, d, d, J=9 Hz, J=3 Hz), 8.73 (1H, d, J=9 Hz), 8.87 (1H, d, J=3 Hz), 10.64 (1H, s), 11.98 (1H, broad s).

(2) 22.0 g of N-(2-fluoroacetamido-5-nitrobenzoyl)-2-methyl-4-chloroaniline are dissolved in 170 ml of acetic acid, and 20 g of boron trifluoride etherate are added thereto. The mixture is stirred at 95° to 100° C. for 30 minutes. The mixture is cooled and concentrated under reduced pressure to remove acetic acid. Water is added to the residue and the mixture is neutralized with sodium bicarbonate. The mixture is extracted with chloroform, and the extract is washed with water, dried and then concentrated to dryness under reduced pressure. Isopropanol is added to the crystalline residue and the crystals are collected therefrom. The thus-obtained crystals are recrystallized from a mixture of dimethylformamide and ethanol (1:2). 18.5 g of 2-fluoromethyl-3-(2-methyl-4-chlorophenyl)-6-nitro-4(3H)-quinazolinone are obtained as colorless prisms.

M.p. 190°–192° C.

NMR (DMSO-d$_6$) δ: 2.13 (3H, s), 5.11 (2H, d, J=45 Hz), 7.30–7.82 (3H, m), 8.00 (1H, d, J=9 Hz), 8.30 (1H, d, d, J=9 Hz, J=2 Hz), 8.83 (1H, d, J=2 Hz).

(3) 17.5 g of 2-fluoromethyl-2-(2-methyl-4-chlorophenyl-6-nitro-4(3H)-quinazolinone are suspended in 260 ml of methanol, and a solution of 45.9 g of stannous chloride dihydrate in 39.1 ml of conc. hydrochloric acid is added thereto under ice-cooling and stirring. The mixture is further stirred under ice-cooling for one hour and then stirred at room temperature overnight. The reaction mixture is poured into 1.5 liters of water, and adjusted to pH 4 to 5 with sodium bicarbonate. 500 ml of chloroform are added to the mixture and the mixture is stirred. Insoluble materials are collected by filtration, and washed with chloroform. The chloroform layers of the filtrate and the washings are combined. The chloroform solution is concentrated to dryness under reduced pressure. Isopropanol is added to the residue and crystalline precipitates are collected therefrom. The thus-obtained crystals (14.8 g, M.p. 188°–191° C.) were recrystallized from ethanol. 13.3 g of 2-fluoromethyl-3-(2-methyl-4-chlorophenyl)-6-amino-4(3H)-quinazolinone are obtained as colorless prisms.

M.p. 191°–193° C.

NMR (CDCl$_3$) δ: 2.10 (3H, s), 4.17 (2H, broad s), 4.92 (2H, d, J=46 Hz), 6.94–7.72 (6H, m).

EXAMPLE 3

(1) 3.6 g of N-(2-amino-5-nitrobenzoyl)-2,3-dimethylaniline and 1.82 g of fluoroacetyl chloride are treated in the same manner as described in Example 1-(1), whereby 3.8 g of N-(2-fluoroacetamido-5-nitrobenzoyl)-2,3-dimethylaniline are obtained as colorless needles.

M.p. 236°–239° C. (recrystallized from a mixture of dimethylformamide and ethanol (1:2)).

NMR (DMSO-d$_6$) δ: 2.13 (3H, s), 2.30 (3H, s), 5.05 (2H, d, J=46 Hz), 7.15 (3H, s), 8.43 (1H, d, d, J=9 Hz, J=2 Hz), 8.77 (1H, d, J=9 Hz), 8.91 (1H, d, J=2 Hz), 10.69 (1H, s), 12.17 (1H, broad s).

(2) 3.5 g of N-(2-fluoroacetamido-5-nitrobenzoyl)-2,3-dimethylaniline, 3.0 g of boron trifluoride etherate and 30 ml of acetic acid are treated in the same manner as described in Example 1-(2), whereby 2.8 g of 2-fluoromethyl-3-(2,3-dimethylphenyl)-6-nitro-4(3H)-quinazolinone are obtained as yellow prisms.

M.p. 178°–180° C. (recrystallized from a mixture of dimethylformamide and ethanol (1:2)).

NMR (CDCl$_3$) δ: 2.04 (3H, s), 2.40 (3H, s), 4.94 (2H, d, J=47 Hz), 6.8–7.5 (3H, m), 7.96 (1H, d, J=9 Hz), 8.57 (1H, d, d, J=9 Hz, J=3 Hz), 9.11 (1H, d, J=3 Hz).

(3) 2.0 g of 2-fluoromethyll-3-(2,3-dimethylphenyl)-6-nitro-4(3H)-quinazolinone and 5.4 g of stannous chloride are treated in the same manner as described in Example 1-(3), whereby 1.1 g of 2-fluoromethyl-3-(2,3-dimethylphenyl)-6-amino-4(3H)-quinazolinone are obtained as pale yellow prisms.

M.p. 189°–192° C. (recrystallized from isopropanol).

NMR (CDCl$_3$+DMSO-d$_6$) δ: 2.01 (3H, s), 2.38 (3H, s), 4.60 (2H, broad s), 4.90 (2H, d, J=47 Hz), 6.9–7.7 (6H, m).

EXAMPLE 4

(1) 3.9 g of N-(2-amino-5-nitrobenzoyl)-2-methyl-4-fluoroaniline, 1.6 g of pyridine and 1.96 g of fluoroacetyl chloride are treated in the same manner as described in Example 1-(1), whereby 4.0 g of N-(2-fluoroacetamido-5-nitrobenzoyl)-2-methyl-4-fluoroaniline are obtained as colorless needles.

M.p. 237°–239° C. (recrystallized from a mixture of dimethylformamide and ethanol (1:2)).

NMR (DMSO-$d_6$) δ: 2.25 (3H, s), 5.05 (2H, d, J=47 Hz) 6.8–7.5 (3H, m), 8.44 (1H, d, d, J=10 Hz, J=3 Hz), 8.76 (1H, d, J=10 Hz), 8.91 (1H, d, J=3 Hz), 10.60 (1H, s), 12.05 (1H, broad s).

(2) 4.0 g of N-(2-fluoroacetamido-5-nitrobenzoyl)-2-methyl-4-fluoraniline, 3.5 g of boron trifluoride etherate and 30 ml of acetic acid are treated in the same manner as described in Example 1-(2), whereby 3.0 g of 2-fluoromethyl-3-(2-methyl-4-fluorophenyl)-6-nitro-4(3H)-quinazolinone are obtained as colorless prisms.

M.p. 171°–173° C. (recrystallized from a mixture of dimethylformamide and ethanol (1:4)).

NMR (DMSO-$d_6$) δ: 2.16 (3H, s), 4.99 (2H, d, J=47 Hz), 6.7–7.4 (3H, m), 7.95 (1H, d, J=10 Hz), 8.60 (1H, d, d, J=10 Hz, J=3 Hz), 9.12 (1H, d, J=3 Hz).

(3) 2.0 g of 2-fluoromethyl-3-(2-methyl-4-fluorophenyl)-6-nitro-4(3H)-quinazolinone and 5.4 g of stannous chloride are treated in the same manner as described in Example 1-(3), whereby 1.1 g of 2-fluoromethyl-3-(2-methyl-4-fluorophenyl)-6-amino-4(3H)-quinazolinone are obtained as yellow prisms.

M.p. 193°–196° C. (recrystallized from isopropanol).

NMR (CDCl$_3$+DMSO-$d_6$) δ: 2.10 (3H, s), 4.92 (2H, d, J=47 Hz), 5.20 (2H, broad s), 6.8–7.8 (6H, m).

EXAMPLE 5

(1) 4.2 g of N-(2-amino-5-nitrobenzoyl)-2-methyl-4-bromoaniline, 1.42 g of pyridine and 1.74 g of fluoroacetyl chloride are treated in the same manner as described in Example 1-(1), whereby 4.73 g of N-(2-fluoroacetamido-5-nitrobenzoyl)-2-methyl-4-bromoaniline are obtained as colorless needles.

M.p. 247°–249° C. (recrystallized from a mixture of dimethylformamide and ethanol (1:2)).

NMR (DMSO-$d_6$) δ: 2.27 (3H, s), 5.07 (2H, d, J=47 Hz) 7.1–7.6 (3H, m), 8.45 (1H, d, d, J=9 Hz, J=3 Hz), 8.76 (1H, d, J=9 Hz), 8.90 (1H, d, J=3 Hz), 10.62 (1H, s), 12.00 (1H, broad s).

(2) 4.0 g of N-(2-fluoroacetamido-5-nitrobenzoyl)-2-methyl-4-bromoaniline, 3.0 g of boron trifluoride etherate and 30 ml of acetic acid are treated in the same manner as described in Example 1-(2), whereby 3.6 g of 2-fluoromethyl-3-(2-methyl-4-bromophenyl)-6-nitro-4(3H)-quinazolinone are obtained as pale yellow prisms.

M.p. 208°–210° C. (recrystallized from a mixture of dimethylformamide and ethanol (1:2)).

NMR (CDCl$_3$) δ: 2.15 (3H, s), 4.99 (2H, d, J=47 Hz), 7.07 (1H, d, J=9 Hz), 7.4–7.7 (2H, m), 7.95 (1H, d, J=9 Hz), 8.60 (1H, d, d, J=9 Hz, J=3 Hz), 9.12 (1H, d, J=3 Hz).

(3) 2.4 g of 2-fluoromethyl-3-(2-methyl-4-bromophenyl)-6-nitro-4(3H)-quinazolinone and 5.4 g of stannous chloride are treated in the same manner as described in Example 1-(3), whereby 1.4 g of 2-fluoromethyl-3-(2-methyl-4-bromophenyl)-6-amino-4(3H)-quinazolinone are obtained as pale yellow prisms.

M.p. 194°–196° C. (recrystallized from isopropanol).

NMR (CDCl$_3$) δ: 2.10 (3H, s), 4.80 (2H, broad s) 4.93 (2H, d, J=47 Hz), 7.0–7.7 (6H, m).

EXAMPLE 6

(1) 4.8 g of N-(2-amino-5-nitrobenzoyl)-2-methyl-4-methoxyaniline, 1.9 g of pyridine and 2.32 g of fluoroacetyl chloride are treated in the same manner as described in Example 1-(1), whereby 5.0 g of N-(2-fluoroacetamido-5-nitrobenzoyl)-2-methyl-4-methoxyaniline are obtained as colorless needles.

M.p. 237°–239° C. (recrystallized from a mixture of dimethylformamide and ethanol (1:2)).

NMR (DMSO-$d_6$) δ: 2.23 (3H, s), 3.77 (3H, s), 5.06 (2H, d, J=47 Hz), 6.6–7.4 (3H, m), 8.41 (1H, d, d, J=9 Hz, 7=3 Hz), 8.77 (1H, d, J=9 Hz), 8.91 (1H, d, J=3 Hz), 10.50 (1H, s), 12.19 (1H, broad s).

(2) 4.0 g of N-(2-fluoroacetamido-5-nitrobenzoyl)-2-methyl-4-methoxyaniline, 3.5 g of boron trifluoride etherate and 30 ml of acetic acid are treated in the same manner as described in Example 1-(2)l, whereby 3.3 g of 2-fluoromethyl-3-(2-methyl-4-methoxyphenyl)-6-nitro-4(3H)-quinazolinone are obtained as yellow prisms.

M.P. 190°–192° C. (recrystallized from a mixture of dimethylformamide and ethanol (1:2)).

NMR (DMSO-$d_6$-CDCl$_3$) δ: 2.11 (3H, s), 3.90 (3H, s), 5.03 (2H, d, J=47 Hz), 6.7–7.4 (3H, m), 7.93 (1H, d, J=9 Hz), 8.63 (1H, d, d, J=9 Hz, J=3 Hz), 8.93 (1H, d, J=3 Hz).

(3) 2.1 g of 2-fluoromethyl-3-(2-methyl-4-methoxyphenyl)-6-nitro-4(3H)-quinazolinone and 5.4 g of stannous chloride are treated in the same manner as described in Example 1-(3), whereby 1.3 g of 2-fluoromethyl-3-(2-methyl-4-methoxyphenyl)-6-amino-4(3H)-quinazolinone are obtained as pale yellow prisms.

M.p. 200°–202° C. (recrystallized from isopropanol).

NMR (CDCl$_3$) δ: 2.09 (3H, s), 3.83 (3H, s), 4.13 (2H, broad s), 4.91 (2H, d, J=47 Hz), 6.8–7.3 (4H, m), 7.47 (1H, d, J=3 Hz), 7.61 (1H, d, J=9 Hz).

EXAMPLE 7

(1) 4.5 g of N-(2-amino-5-nitrobenzoyl)-2-methyl-5-fluoroaniline, 1.85 g of pyridine and 2.26 g of fluoroacetyl chloride are treated in the same manner as described in Example 1-(1), whereby 5.2 g of N-(2-fluroacetamido-5-nitrobenzoyl)-2-methyl-5-fluoroaniline are obtained as colorless needles.

M.p. 217°–219° C. (recrystallized from a mixture of dimethylformamide and ethanol (1:2)).

NMR (DMSO-$d_6$) δ: 2.28 (3H, s), 5.09 (2H, d, J=47 Hz), 6.8–7.6 (3H, m), 8.45 (1H, d, d, J=10 Hz, J=3 Hz), 8.76 (1H, d, J=10 Hz), 8.91 (1H, d, J=3 Hz), 10.65 (1H, s), 11.93 (1H, broad s).

(2) 4.3 g of N-(2-fluoroacetamido-5-nitrobenzoyl)-2-methyl-5-fluoroaniline, 3.5 g of boron trifluoride etherate and 30 ml of acetic acid are treated in the same manner as described in Example 1-(2), whereby 3.6 g of 2-fluoromethyl-3-(2-methyl-5-fluorophenyl-6-nitro-4(3H)-quinazolinone are obtained as pale yellow prisms.

This prouct exhibits dimorphism and has melting points at 185°–186° C. and 200°–201° C. (recrystallized from a mixture of dimethylformamide and ethanol (1:2)).

NMR (DMSO-$d_6$) δ: 1.25 (3H, s), 5.06 (2H, d, J=46 Hz), 7.0–7.8 (3H, m), 7.97 (1H, d, J=10 Hz), 8.62 (1H, d, d, J=10 Hz, J=3 Hz), 9.04 (1H, d, J=3 Hz).

(3) 2.0 g of 2-fluoromethyl-3-(2-methyl-5-fluorophenyl)-6-nitro-4(3H)-quinazolinone and 5.4 g of stannous chloride are treated in the same manner as described in Example 1-(3), whereby 1.2 g of 2-fluoromethyl-3-(2-methyl-5-fluorophenyl)-6-amino-4(3H)-quinazolinone are obtained as pale yellow prisms.

M.p. 174°–176° C. (recrystallized from isopropanol).

NMR (CDCl$_3$) δ: 2.10 (3H, s), 4.16 (2H, broad s), 4.95 (2H, d, J=47 Hz), 6.8–7.8 (6H, m).

EXAMPLE 8

(1) 4.0 g of N-(2-amino-5-nitrobenzoyl)-2-methyl-5-chloroaniline, 1.54 g of pyridine and 1.88 g of fluoroacetyl chloride are treated in the same manner as described in Example 1-(1), whereby 4.5 g of N-(2-fluoroacetamido-5-nitrobenzoyl)-2-methyl-5-chloroaniline are obtained as pale yellow needles.

M.p. 210°–212° C. (recrystallized from a mixture of dimethylformamide and ethanol (1:2)).

NMR (DMSO-d$_6$) δ: 2.28 (3H, s), 5.09 (2H, d, J=47 Hz), 7.2–7.6 (3H, m), 8.46 (1H, d, d, J=10 Hz, J=3 Hz), 8.75 (1H, d, J=10 Hz), 8.91 (1H, d, J=3 Hz), 10.67 (1H, s), 11.91 (1H, broad s).

(2) 4.0 g of N-(2-fluoroacetamido-l5-nitrobenzoyl)-2-methyl-5-chloroaniline, 3.5 g of boron trifluoride etherate and 30 ml of acetic acid are treated in the same manner as described in Example 1-(2), whereby 3.4 g of 2-fluoromethyl-3-(2-methyl-5-chlorophenyl)-6-nitro-4(3H)-quinazolinone are obtained as pale yellow needles.

M.p. 191°–192° C. (recrystallized from a mixture of dimethylformamide and ethanol (1:2)).

NMR (CDCl$_3$) δ: 2.15 (3H, s), 5.01 (2H, d, J=47 Hz), 7.2–7.6 (3H, m), 7.95 (1H, d, J=9 Hz), 8.60 (1H, d, d, J=9 Hz, J=3 Hz), 9.11 (1H, d, J=3 Hz).

(3) 2.14 g of 2-fluoromethyl-3-(2-methyl-5-chlorophenyl)-6-nitro-4(3H)-quinazolinone and 5.4 g of stannous chloride are treated in the same manner as described in Example 1-(3), whereby 1.0 g of 2-fluoromethyl-3-(2-methyl-5-chlorophenyl)-6-amino-4(3H)-quinazolinone is obtained as pale yellow prisms.

M.p. 214°–216° C. (recrystallized from isopropanol).

NMR (CDCl$_3$+DMSO-d$_6$) δ: 2.09 (3H, s), 4.93 (2H, d, J=47 Hz), 5.18 (2H, broad s), 7.0–7.8 (6H, m).

Preparation of Starting Compounds

A mixture of 4.16 g of 5-nitroisatoic anhydride, 3.6 g of 2,4-dimethylaniline and 25 ml of xylene is refluxed for 30 minutes with heating. After the reaction is completed, the reaction mixture is cooled and crystalline precipitates are collected therefrom. The thus-obtained crystals are recrystallized from a mixture of dimethylformamide and ethanol, whereby 4.7 g of N-(2-amino-5-nitrobenzoyl)-2,4-dimethylaniline are obtained as yellow needles.

Yield: 82%.

M.p. 209°–210° C.

The following compounds are obtained in the same manner as described above.

N-(2-amino-5-nitrobenzoyl)-2-methyl-4-chloroaniline
  Yield: 71%. M.p. 219°–221° C.

N-(2-amino-5-nitrobenzoyl)-2,3-dimethylaniline
  Yield: 69%. M.p. 238°–240° C.

N-(2-amino-5-nitrobenzoyl)-2-methyl-4-fluoroaniline
  Yield: 60%. M.p. 241°–243° C.

N-(2-amino-5-nitrobenzoyl)-2-methyl-4-bromoaniline
  Yield: 74%. M.p. 228°–229° C.

N-(2-amino-5-nitrobenzoyl)-2-methyl-4-methoxyaniline
  Yield: 77%. M.p. 195°–196° C.

N-(2-amino-5-nitrobenzoyl)-2-methyl-5-fluoroaniline
  Yield: 68%. M.p. 216°–217° C.

N-(2-amino-5-nitrobenzoyl)-2-methyl-5-chloroaniline
  Yield: 70%. M.p. 248°–250° C.

What we claim is:

1. 2-Fluoromethyl-3-(2-methyl-4-chlorophenyl)-6-amino-4(3H)-quinazolinone or a pharmaceutically acceptable acid addition salt thereof.

2. A pharmaceutical composition which comprises a pharmaceutically effective amount of 2-fluoromethyl-3-(2-methyl-4-chlorophenyl)-6-amino-4(3H)-quinazolinone or a pharmaceutically acceptable acid addition salt thereof and pharmaceutically acceptable carrier therefor.

* * * * *